United States Patent [19]

Tanigaki et al.

[11] Patent Number: 5,185,257
[45] Date of Patent: Feb. 9, 1993

[54] **THERMOSTABLE XANTHINE OXIDASE FROM *ARTHROBACTER LUTEUS***

[75] Inventors: Naoko Tanigaki; Kayoko Furukawa; Yukihiro Sogabe; Shigenori Emi, all of Tsuruga, Japan

[73] Assignee: Toyo Boseki Kabushiki Kaisha, Osaka, Japan

[21] Appl. No.: 686,237

[22] Filed: Apr. 16, 1991

[30] Foreign Application Priority Data

Apr. 18, 1990 [JP] Japan .................................. 2-104054

[51] Int. Cl.$^5$ .......................... C12N 9/06; C12N 1/00
[52] U.S. Cl. ..................................... 435/191; 435/830
[58] Field of Search .............................. 435/191, 830

[56] References Cited

U.S. PATENT DOCUMENTS

| | | | |
|---|---|---|---|
| 3,716,452 | 2/1973 | Kitamura et al. | 435/206 |
| 4,172,763 | 10/1979 | Zikakis | 435/191 |
| 4,238,566 | 12/1990 | Zikakis | 435/191 |
| 4,341,868 | 7/1982 | Nakanishi et al. | 435/191 |

OTHER PUBLICATIONS

Woolfolk et al, J. of Bacteriology, vol. 135, No. 2, pp. 422–428, 1978.
Woolfolk et al, J. of Bacteriology, vol. 130, No. 3, pp. 1175–1191, 1977.
Machida et al, Agric. Biol. Chem., vol. 45, No. 2, pp. 425–432, 1981.

*Primary Examiner*—David M. Naff
*Assistant Examiner*—Mike Meller
*Attorney, Agent, or Firm*—Leydig, Voit & Mayer

[57] ABSTRACT

A new thermostable xanthine oxidase obtained from a microbe belonging to the genus Arthrobacter and a method of its production are disclosed. The present invention affords a xanthine oxidase which is excellent in thermal stability and which retains at least 70% residual activity after heat treatment at 60° C. for 30 minutes. *Arthrobacter luteus* ATCC 21606 is the preferred microbe. The enzyme has a molecular weight of about 160,000 daltons as determined by gel filtration and a pH optimum of about 7.5.

11 Claims, 3 Drawing Sheets

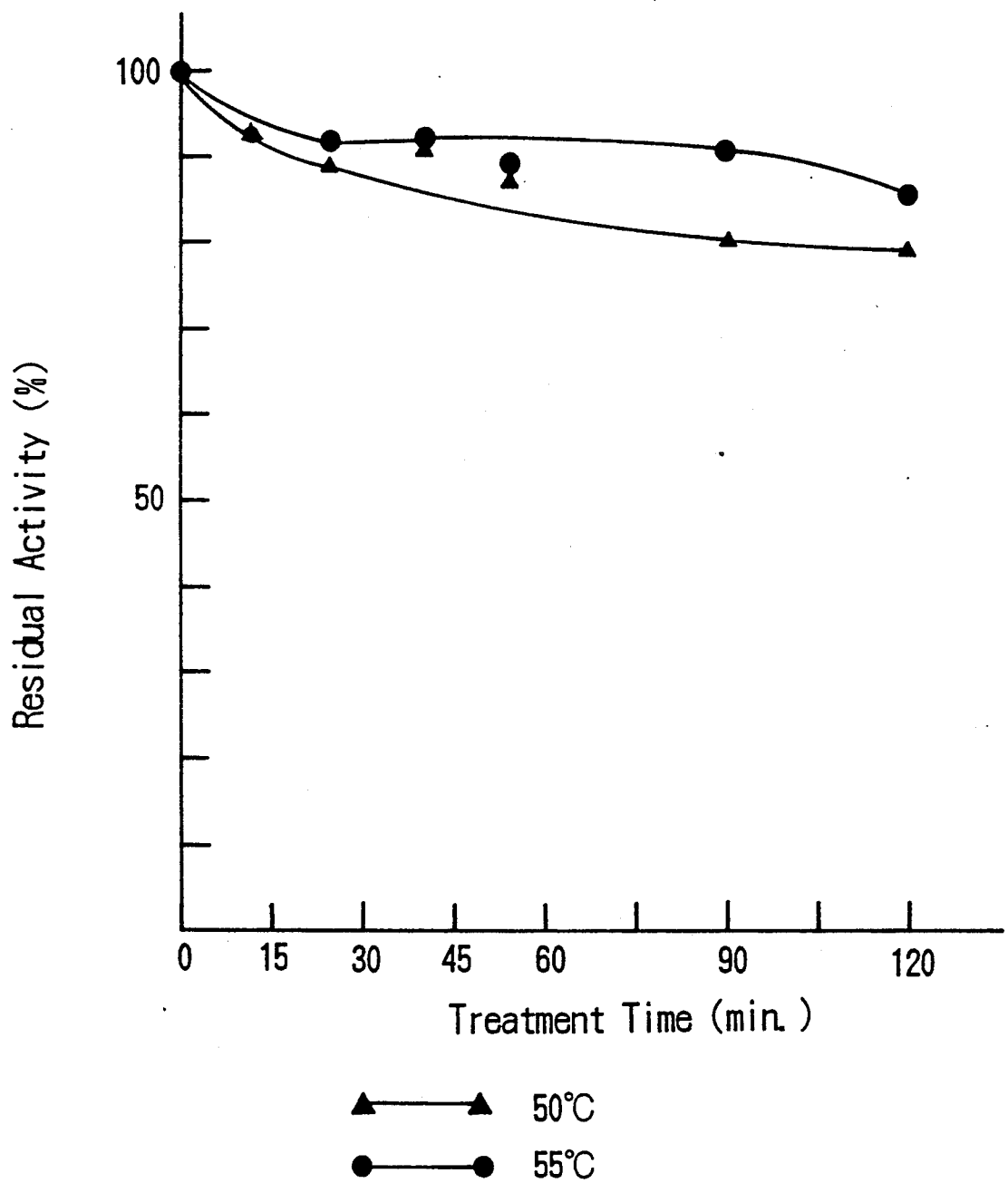

THERMOSTABLE XANTHINE OXIDASE FROM *ARTHROBACTER LUTEUS*

BACKGROUND OF THE INVENTION

The present invention relates to a new thermostable xanthine oxidase and a method of its production. The xanthine oxidase of the present invention is an enzyme which catalyzes the reaction in which hypoxanthine and xanthine are oxidized into hydrogen peroxide, and it is characterized by excellent thermal stability.

The xanthine oxidase of the present invention is used to quantitatively determine inorganic phosphorus which serves as an index of, for example, nephritis and thyropathy, adenosine deaminase which serves as an index of immune diseases, and other substances.

Heretofore, xanthine oxidase has been known to be present in cow's milk, but quantitative determination of the xanthine oxidase derived from cow's milk on the basis of hydrogen peroxide wherein the xanthine oxidase is allowed to act on a sample containing hypoxanthine and xanthine and the resulting hydrogen peroxide is converted to a pigment has been unattainable because the pigment is decomposed in a short time.

In addition, microbial xanthine oxidase enzymes have been known, including those derived from microbes belonging to Pseudomonas, Escherichia, Arthrobacter, Nocardia and other genera [J. Bacteroiology, 130, 1175 (1977); J. Bacteriol., 135, 422 (1978)] and the xanthine oxidase enzyme derived from *Enterobacter cloacae* [A.B.C., 45, 425 (1981)], but none of them have sufficient activities or thermal stability.

SUMMARY OF THE INVENTION

Taking note of the situation described above, the present inventors have attempted to find a xanthine oxidase which surpasses conventional xanthine oxidases in thermal stability.

With the aim of solving the problems described above, the present inventors have made intensive investigations, and found a xanthine oxidase possessing excellent thermal stability from a microbe belonging to the genus Arthrobacter.

Specifically, the present invention provides a thermostable xanthine oxidase which shows substrate specificity to at least hypoxanthine and xanthine and which catalyzes the reaction in which hypoxanthine is oxidized into xanthine which is further oxidized into uric acid (see the following reaction formulas) to form hydrogen peroxide in the presence of oxygen as the electron recipient, characterized by retention of at least 70% residual activity after heat treatment at 60° C. for 30 minutes.

Reaction Formulas

Hypoxanthine + $O_2 \rightarrow$ xanthine + $H_2O_2$
Xanthine + $O_2 \rightarrow$ uric acid + $H_2O_2$ Further, the present invention provides a production method for thermostable xanthine oxidase characterized by cultivating in nutrient medium a bacterial strain belonging to the genus Arthrobacter which is capable of producing thermostable xanthine oxidase and subsequently collecting the thermostable xanthine oxidase from the resulting culture.

BRIEF DESCRIPTION OF THE DRAWINGS

FIG. 3 shows the relationship between heat treatment time and residual activity at 50° and 55° C. in the xanthine oxidase of the present invention.

DETAILED DESCRIPTION OF THE INVENTION

Figure 1:
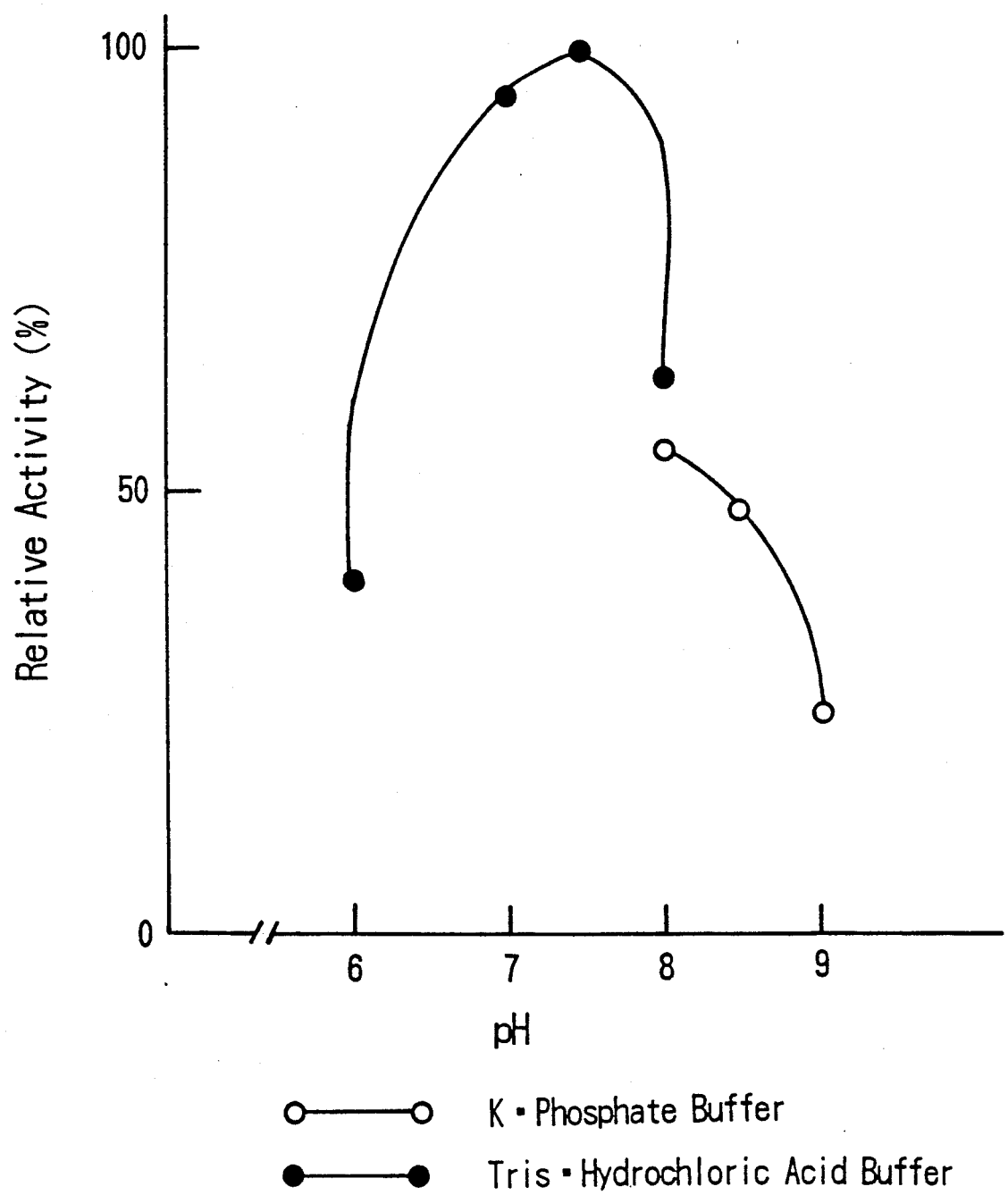
FIG. 1 shows the optimum pH of the xanthine oxidase of the present invention.

The microbe used for the present invention includes bacteria of the genus Arthrobacter which are capable of producing xanthine oxidase having the properties described above. Examples of preferred microbes include *Arthrobacter luteus*, accession number ATCC 21606, American Type Culture Collection, 12301 Park Lawn Drive, Rockville, Md. 20852-1776.

In producing the enzyme of the present invention, a xanthine oxidase producer bacterium is cultivated by an ordinary method of enzyme production. Any culture medium, whether it is synthetic or natural, can be used, as long as it contains appropriate amounts of a carbon source, a nitrogen source, inorganic substances and other necessary nutrients which can be assimilated by the strain. Also, it is desirable to add nucleic acid substances such as hypoxanthine and xanthine as xanthine oxidase production inducers to the medium.

Cultivation is normally carried out by shaking culture or aerobic submerged culture, preferably at 30° to 40° C. Cultivation can be carried out under conditions other than those mentioned above, as long as the strain used can grow thereunder. Growth usually occurs in a cultivation period of usually 1 to 2 days, during which xanthine oxidase is produced and accumulated in bacterial cells.

The enzyme of the present invention can be purified by ordinary purification methods. For example, extraction can be achieved by any means such as ultrasonic disruption, mechanical disruption using glass beads, French press, or a surfactant. The obtained extract can be purified by salting-out with ammonium sulfide or Glauber's salt, metal coagulation using magnesium chloride or calcium chloride, coagulation using protamine or ethylene imine polymer, ion exchange chromatography and other methods.

The determination methods for the activity of the xanthine oxidase of the present invention are described below.

Determination Method I 50 mM tris-hydrochloric acid buffer (2.9 ml) and 0.1 ml of a 10 mM aqueous solution of xanthine are mixed, and this mixture is pre-heated at 37° C. After 0.01 ml of enzyme solution is added and gently mixed, the increase of absorbance at 293 nm per minute is determined using a spectrophotometer thermostated at 37° C. with distilled water as the control. The xanthine oxidase activity is expressed on the assumption that the amount of enzyme which produces 1 μmol of uric acid per minute under the conditions described above is taken as 1 unit (U).

Determination Method II 50 mM tris-hydrochloric acid buffer (2.1 ml), 0.25 ml of 0.15% 4-aminoantipyrine, 0.25 ml of 0.3% N-ethyl-N-(2-hydroxy-3-sulfopropyl)-m-toluidine (TOOS), 0.4 ml of 50 U/ml peroxidase and 0.1 ml of a 5 mM aqueous solution of hypoxanthine are mixed, and this mixture is pre-heated at 37° C. After 0.01 ml of enzyme solution is added and gently mixed, the increase of absorbance at 550 nm per minute is determined using a spectrophotometer thermostated at 37° C. with distilled water as the control. The xanthine oxidase activity is expressed on the assumption that the amount of enzyme which produces 1 μmol of quinone imine pigment per minute under the conditions described above is taken as 1 unit (U).

The physical and chemical properties of an example of the enzyme of the present invention are described below.

(1) Thermal stability

The enzyme (0.8 U/ml) of the invention was treated in 50 mM tris-hydrochloric acid buffer (pH 8.0) at various temperatures (0°, 37°, 40°, 45°, 50°, 55°, 60°, 65° and 70° C.) for 30 minutes and then cooled with ice for 5 minutes, and the xanthine oxidation residual activity was determined by the determination method I. The enzyme was found to be stable up to 55° C., with a residual activity of about 80% retained at 60° C. (see FIG. 2).

The activity of the enzyme of the present invention was determined after heat treatment at 50° and 55° C. for various treatment times; the results are shown in FIG. 3.

(2) Optimum pH

The optimum pH for the enzyme of the present invention was found to be nearly 7.5.

(3) km value

The km value of the enzyme of the present invention was found to be about $5.2 \times 10^{-5}$M for hypoxanthine and about $5.4 \times 10^{-5}$M for xanthine at pH 7.5.

(4) Molecular weight

The molecular weight of the enzyme of the present invention was determined by gel filtration (TOYO SODA, TSK-GEL G3000 SW column) to be about 160,000.

(5) pH range for stability

The pH range for the stability of the enzyme of the present invention was found to be between 6.0 and 9.0.

The enzyme of the present invention is excellent in quantitative determination of the substrate on which it acts in comparison with the conventional xanthine oxidase derived from cow's milk. That is, the enzyme of the present invention offers stable color development in a chromogenic system in which the enzyme of the present invention is allowed to act on xanthine or hypoxanthine in the presence of oxygen as the electron recipient and the resulting hydrogen peroxide is converted to a pigment. Comparison of the enzyme of the present invention with conventional microbial xanthine oxidase (U.S. Pat. No. 4,341,868) as to heat stability shows that the enzyme of the present invention surpasses the conventional enzymes in thermal stability in view of about 80% residual activity of the enzyme of the present invention after heat treatment at 60° C. for 30 minutes as compared with 30% residual activity of the enzyme from *Enterobacter cloacae* and 40% residual activity of the known enzyme from Arthrobacter (Toyojozo Co., Ltd.).

The present invention is hereinafter described in more detail by means of the following examples.

EXAMPLE 1

To a 30-ml test tube was transferred 5 ml of a medium (pH 7.0) containing 0.3% polypeptone, 0.3% meat extract, 0.3% yeast extract, 0.1% $KH_2PO_4$, 0.22% $K_2HPO_4$, 0.5% $MgSO_4 7H_2O$ and 0.1% hypoxanthine, and this test tube was autoclaved at 121° C. for 15 minutes. As the seed inoculant, a platinum loopful of *Arthrobacter luteus* ATCC 21606 was inoculated and subjected to shaking culture at 30° C. for 18 hours to give a seed culture broth. The same medium (250 ml) was dispensed to four 2-l Sakaguchi flasks and autoclaved at 121° C. for 15 minutes. To each flask was transferred 5 ml of the seed culture broth, which was followed by shaking culture at 30° C. for 24 hours. The xanthine oxidase activity upon completion of the cultivation was 40 mU per ml culture broth.

Figure 2:
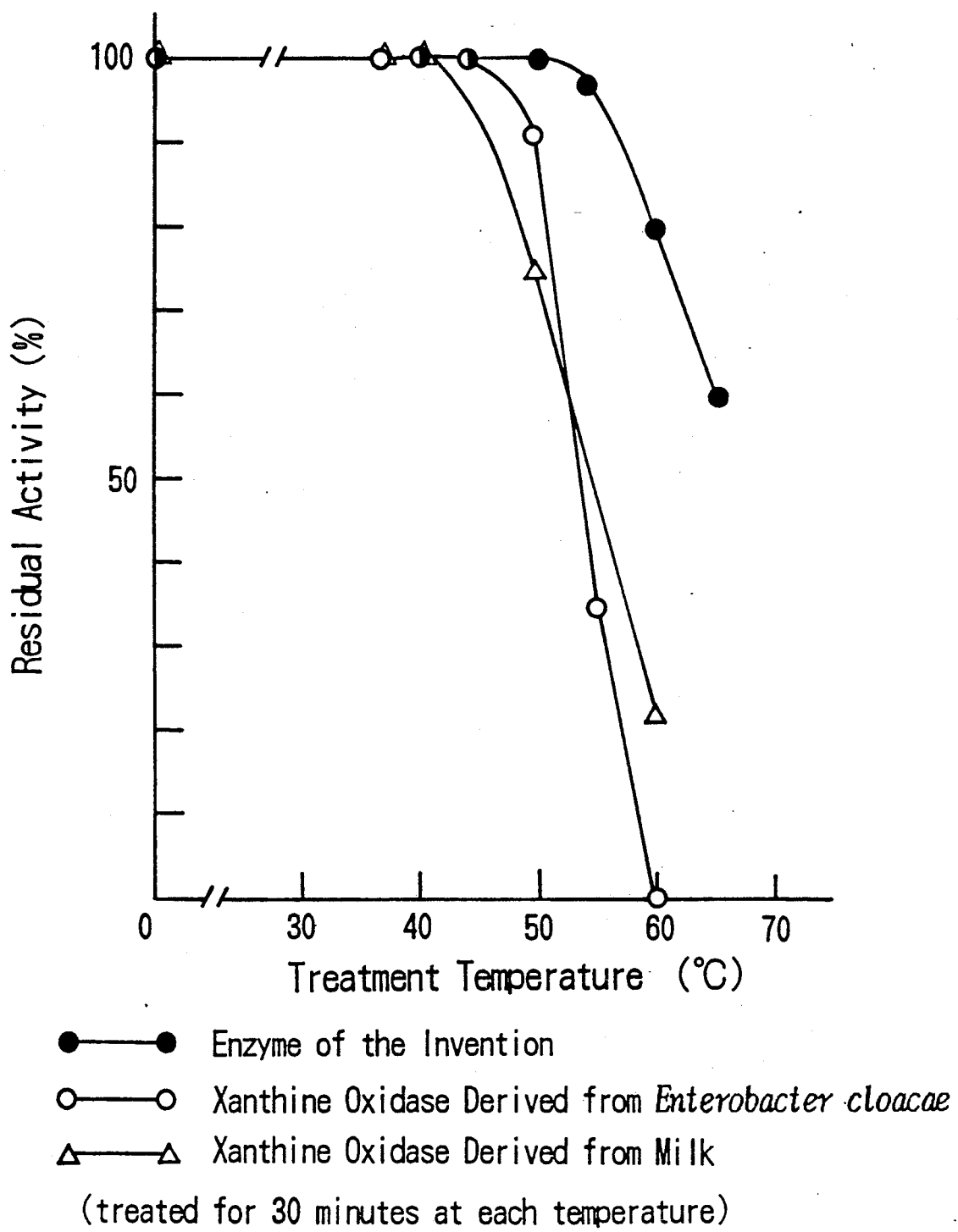
FIG. 2 compares thermal stability of the xanthine oxidase of the present invention, that of the xanthine oxidase derived from *Enterobacter cloacae* and that of the xanthine oxidase derived from milk.

After 1 l of the culture broth was centrifuged, cells were harvested and suspended in 100 ml of 50 mM tris-hydrochloric acid buffer (pH 8.0). This suspension was treated using an ultrasonic disrupter (SONIFIER, product of BRANSON) for 10 minutes, followed by centrifugation to give 102 ml of a supernatant. This supernatant was subjected to ethylene imine polymer treatment and salting-out with ammonium sulfate to yield a salting-out precipitate. This precipitate was suspended in 50 mM tris-hydrochloric acid buffer, followed by centrifugation to give a supernatant. This supernatant was desalted with Sephadex G-25 (product of Pharmacia) equilibrated with 50 mM tris-hydrochloric acid buffer. Then, the supernatant was subjected to column chromatography with DEAE-Sepharose CL-6B (product of Pharmacia) equilibrated with the same buffer. The xanthine oxidase activity was detected in the fraction eluted from 0 to 0.5M NaCl. The eluate was desalted using Sephadex G-25 to afford 13.8 U of enzyme. The physical and chemical properties of the obtained enzyme are shown in Table 1. The determination results of its thermal stability are shown in FIG. 2.

COMPARATIVE EXAMPLE

Determinations were made for conventional xanthine oxidase derived from milk and xanthine oxidase derived from *Enterobacter cloacae*. Their physical and chemical properties are shown in Table 1. The determination results of their thermal stability are shown in FIG. 2.

TABLE 1

| | Properties | | | | | |
|---|---|---|---|---|---|---|
| | Substrate assayability | km value | | Optimum | Thermal stability | Molecular |
| Enzyme | (chromogenic system) | hypoxanthine | xanthine | pH | (60° C., 30 min.) | weight |
| Example | | | | | | |
| enzyme of the invention | 100% | $5.2 \times 10^{-5}$ M | $5.4 \times 10^{-5}$ M | 7.5 | 80% | 160,000 |
| Comparative Example | | | | | | |

TABLE 1-continued

| Enzyme | Properties | | | | | |
|---|---|---|---|---|---|---|
| | Substrate assayability (chromogenic system) | km value | | Optimum pH | Thermal stability (60° C., 30 min.) | Molecular weight |
| | | hypoxanthine | xanthine | | | |
| xanthine oxidase derived from *Enterobacter cloacae* | 100% | $8.3 \times 10^{-5}$ M | $7.3 \times 10^{-5}$ M | 7.0 | 0% | 128,000 |
| xanthine oxidase derived from milk | 80% | $1.3 \times 10^{-6}$ M | $1.7-3.6 \times 10^{-6}$ M | 8.2 | 30% | 275,000 |

EXAMPLE 2

An enzyme obtained in the same manner as in Example 1 was heat-treated at 50° and 55° C. for various treatment times, and its thermal stability was determined. The results are shown in FIG. 3.

The present invention affords a xanthine oxidase which is excellent in thermal stability and which retains at least 70% residual activity after heat treatment at 60° C. for 30 minutes.

What is claimed is:

1. An isolated thermostable xanthine oxidase which shows substrate specificity to at least hypoxanthine and xanthine and which catalyzes the reaction wherein hypoxanthine is oxidized into xanthine which is further oxidized into uric acid to form hydrogen peroxide in the presence of oxygen as the electron recipient, characterized by retention of at least 70% residual activity after treatment at 60° C. for 30 minutes, has a molecular weight of about 160,000 daltons as determined by gel filtration, a pH range for stability between 6.0 and 9.0 and an optimum pH of about 7.5.

2. The thermostable xanthine oxidase as claimed in claim 1, which exhibits at least 80% residual activity after treatment at 60° C. for 30 minutes.

3. The thermostable xanthine oxidase as claimed in claim 1, which exhibits at least 90% residual activity after treatment at 50° C. for 30 minutes.

4. The thermostable xanthine oxidase as claimed in claim 1, which is derived from microbes belonging to the genus Arthrobacter.

5. The thermostable xanthine oxidase as claimed in claim 4, wherein the microbe belonging to the genus Arthrobacter is *Arthrobacter luteus* ATCC 21606.

6. A thermostable xanthine oxidase isolated from *Arthrobacter luteus* ATCC 21606 which shows substrate specificity to at least hypoxanthine and xanthine and which catalyzes the reaction wherein hypoxanthine is oxidized into xanthine which is further oxidized into uric acid to form hydrogen peroxide in the presence of oxygen as the electron recipient, characterized by retention of at least 70% residual activity after treatment at 60° C. for 30 minutes.

7. The thermostable xanthine oxidase of claim 6, which exhibits at least 80% residual activity after treatment at 60° C. for 30 minutes.

8. The thermostable xanthine oxidase of claim 6, which exhibits at least 90% residual activity after treatment at 50° C. for 30 minutes.

9. The thermostable xanthine oxidase of claim 6, which has a molecular weight of about 160,000 daltons as determined by gel filtration.

10. The thermostable xanthine oxidase of claim 6, which has an optimum pH of about 7.5.

11. The thermostable xanthine oxidase of claim 6, wherein the pH range for the stability thereof is between 6.0 and 9.0.

* * * * *